(12) United States Patent
Herzberg et al.

(10) Patent No.: US 6,544,205 B1
(45) Date of Patent: Apr. 8, 2003

(54) CLAVICLE BANDAGE

(75) Inventors: Thorsten Herzberg, Hamburg (DE); John Shanahan, Tipperary (IE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/639,292

(22) Filed: Aug. 15, 2000

(30) Foreign Application Priority Data

Aug. 17, 1999 (DE) .......................... 199 39 005

(51) Int. Cl.[7] .................. A61F 5/00; A61F 5/02
(52) U.S. Cl. .................. 602/19; 2/45; 128/DIG. 19
(58) Field of Search ................ 602/5, 19, 20, 602/60–62, 4; 128/869, 876, DIG. 19; 2/45

(56) References Cited

U.S. PATENT DOCUMENTS

| 370,055 | A | * | 9/1887 | Haley | |
| 3,382,868 | A | | 5/1968 | Stiefel | 128/87 |
| 3,718,137 | A | | 2/1973 | Gaylord, Jr. | 128/87 R |
| 3,856,004 | A | | 12/1974 | Cox | 128/87 R |
| 3,897,776 | A | | 8/1975 | Gaylord, Jr. | 128/87 R |
| 4,589,406 | A | | 5/1986 | Florek | 128/87 |
| 5,133,340 | A | | 7/1992 | Koopman | 602/19 |

FOREIGN PATENT DOCUMENTS

| DE | 259 349 | 5/1912 | |
| DE | 89 00 721 | 5/1989 | ........... A61F/13/14 |
| DE | 42 36 654 A1 | 5/1994 | ........... A61F/13/14 |
| DE | 297 20 920 U1 | 3/1998 | ........... A61F/5/02 |
| DE | 298 08 357 U1 | 10/1998 | ........... A61F/13/14 |
| EP | 0 379 929 B1 | 12/1992 | ........... A61F/5/04 |

* cited by examiner

Primary Examiner—Denise M. Pothier
(74) Attorney, Agent, or Firm—Norris McLaughlin & Marcus

(57) ABSTRACT

A clavicle bandage having two adjustable-length strips made from non-extensible material, wherein the free ends of the strips form loops about a ring and wherein the other ends of the strips fasten to the ring by a material pocket and are fixed at an angle relative to one another by the material pocket. The ring has a flat, elliptical cross-section and freely rotates within the material pocket. The strips are fixed at an angle from sixth to eighty degrees.

8 Claims, 4 Drawing Sheets

CLAVICLE BANDAGE

BACKGROUND OF THE INVENTION

The invention relates to a medical bandage for treating injuries, especially fractures of the collarbone (clavicle).

Fractures of the collarbone and other injuries to it are treated predominantly by means of bandages or dressings. A known dressing is the "backpack" dressing, in which, for example, a stockinette sleeve is filled with wadding and cut to appropriate length. This filled sleeve is applied to the neck region of the patient, passed over both collarbones and armpits, and knotted on the back.

A disadvantage of this kind of bandage is that is has to be produced within the hospital itself, which proves to be very time-consuming. Moreover, the dressing is extensible, i.e., it lengthens under tension, as a result of which the dressing has to be readjusted several times in the course of the treatment in order to position the collarbone fragments firmly. Finally, there is the risk that, owing to the knot in the back region, skin irritations or even injuries may arise. A further complicating factor is that the dressing is not particularly sweat-absorbing. Excessive perspiration under the dressing may therefore lead to further instances of skin irritation.

U.S. Pat. No. 3,856,004 discloses a clavicle bandage formed essentially from one strip. The strip is divided centrally, except for a small end piece, into two straps. At the end of the incision between the straps, there is an equilateral triangle which is sited on the back of the patient and through which, with the bandage applied, the straps are drawn and fixed to themselves by means of touch-and-close fastenings.

U.S. Pat. No. 3,897,776 describes a clavicle bandage similar to that known from U.S. Pat. No. 3,856,004. The bandage is formed by two straps which are fastened on the back with the aid of an approximately right-angled triangle.

DE 259 349 discloses a device referred to as a "straightener" which comprises two arm loops which come together at the back, the ends, which run backwards above the shoulders, being held by a fixed ring. Hanging from the ring is an elastic strap which has a loop at the bottom end through which the two other ends, extending backwards below the shoulders and fitted with adjustable loops, are passed crosswise.

The bandages or dressings described, however, are able to fulfil the requirements imposed on them only to a limited extent. In some cases they are very complex to produce, cannot be retensioned adequately, and have fastenings which are expensive and are awkward to operate.

DE 298 08 357 presents a clavicle bandage whose principal constituent comprises two strips which, starting from a fastening point of a back part, are passed each over one shoulder of the patient on the front side of the body and, from there, under the armpits through to the said fastening point on the back part. In the chest region, the strips are connected to one another by a tension element, the length of the tension element being calculated and adjustable such that the strips are guided towards the middle of the body.

EP 0 379 929 B1 specifies clavicle bandages formed from two straps which are adjustable in their length. At their free ends, the straps have means for forming loops. With their other end, the straps, independently of one another, are fastened to a ring, which is preferably configured with a flat cross section. Furthermore, the strips consist of essentially unstretchable material. With the bandage applied, pads may be present on the bandage in the region of the armpits. When the bandage is applied, these straps exert pressure on the clavicle and are joined to one another on the back.

The construction as mentioned in EP 0379 929 B1 has established itself over a long period of time. It has been found, however, that the straps coming from the back are usually positioned poorly or inaccurately and, in the applied state, increasingly wander to the sides, so substantially impairing both function and wear comfort. In the region of the medial scapular spine, the ring leads to pressure points and, owing to partial deformation, to a loss of stability of the bandage. Moreover, the nature and configuration of the armpit pads are capable of improvement, since pressure points often occur in the axillary region and the arms are forced into an abduction position, which is often manifested in pain, brought about by pressure on the axillary nerves.

SUMMARY OF THE INVENTION

It is an object of the invention to develop a clavicle bandage which, derived from the traditional stockinette sleeve backpack dressing, does not have the abovementioned defects. In particular, the bandage should be uncomplicated to apply and offer a high level of wear comfort, being easy to readjust if necessary.

This object is achieved by means of a clavicle bandage as set out in the main claim. The subclaims relate to advantageous further developments of the clavicle bandage.

The invention accordingly provides a clavicle bandage having two adjustable-length strips which at their free ends have means of forming loops, the strips, which essentially comprise non-extensible material, each being fastened by their other end to a ring and being fixed in their position relative to one another by a material pocket.

The strips preferably comprise a laminated foam material. It has proved to be advantageous if the strips exhibit a high cushioning effect under load of approximately 50 N and a preferred longitudinal extension of less than 35%, with particular preference a longitudinal extension of less than 10%.

The ring has a flat elliptical cross section and/or an elliptical profile. Consequently, when the bandage is applied, the ring lies flat, owing indeed to the elliptical profile, so that angular pressure or edge pressure of the ring on the back of the patient is avoided. Furthermore, the profiling of the ring increases the stability, and deformation of the ring in the applied state is not observed.

The ring should comprise customary plastics such as polypropylene or polyethylene in order to minimize allergic reactions on the skin.

In a first preferred embodiment, the means of forming loops comprise a touch-and-close system.

With further preference, the touch-and-close system is designed such that the free end of the strips, on their outer surface facing away from the body, carries a hook section which forms one closure part of the touch-and-close fastening and comprises outwardly directed hooks disposed at a distance from one another, and such that, subsequently, at least one subsection of the outer surface carries hookable material which functions as the other part of the touch-and-close fastening by virtue of the fact that the hooks are able to adhere to it.

The hookable subsection may account for at least one sixth of the length of the strips. In an alternative embodiment, the strips, on their outer surface facing away from the body, comprise over their whole length a material to which the hooks of the other closure part adhere.

For the purpose of fixing the strips on the ring, the material pocket, which is formed from a section of material turned over the ring, advantageously possesses the form of an irregular pentagon, so that the angle α between the strips going away from the ring is from 50° to 95°, in particular 68°.

The fixing is normally accomplished by the stitching of the material pocket to the strips. By virtue of the formation of such a pocket, improved strap passage in comparison to the known bandages is achieved when the bandage is applied, the cranial tip of the pentagon being higher than in known bandages, and/or closer to the neck region of the patient. In its optimum position, the ring ends in the region below the seventh cervical vertebra, in particular between the first four thoracic vertebrae (thoracic vertebrae Th1 to Th4).

The fastening of the strap by means of the material pocket counteracts sideways movement of the strips in the frontal region. In addition, this type of fastening results in a cushioning of the elliptical ring.

In a further advantageous embodiment of the clavicle bandage of the invention, the strips, approximately in the central section of their inner side facing the body, have a pad comprising a sweat-absorbing material such as nylon, polyester and/or cotton, preferably cotton.

The pad in the region of the axillae comprises in particular a spacer knit with a thickness of 3.5 mm to 15 mm, preferably 5 mm, and with a basis weight of from 200 to 1000 g/m$^2$, preferably from 300 to 800 g/m$^2$; with further preference the surface of that side of the pad which faces the axillary part is roughened, similar to a fleece, so as to give an optimum cushioning effect. The roughening of the surface produces a particularly soft surface.

The high air permeability of the spacer knit, especially with the roughened surface, provides for effective breathing of the skin, and the perspiration is transported from the surface to the interior of the bandage strip.

Despite the very high cushioning effect, the risk of heat accumulation is avoided. To increase this effect further, the axillary pads, on the surface facing the skin, may also comprise special fibres which, similar to a wick, transport the perspiration from the body side towards the strap, such as DuPont's COOLMAX®, a DACRON® polyester fabric.

In a further embodiment, the axillary pads may consist of a spacer woven which possesses an additional lining on the side facing the axillary part.

The bandage may be offered in different sizes. The total length varies from about 1 m to 2.1 m, the hook sections on the strips taking up from approximately 10 to 15 cm. The cushioning sections extend over from 15 to 45 cm, in particular over from 25 to 35 cm. The strips of the clavicle bandage preferably do not exceed a thickness of 2 cm. The ring has an external diameter of 8 cm and an internal diameter of 6 cm, the ring having centrally a height of from 0.35 cm to 0.60 cm, preferably from 0.40 cm to 0.50 cm.

In therapy, surprisingly and unexpectedly, the bandage shows a very high gain in benefit over those known to date. Irritation of the skin on the back below the ring is not observed, although the ring lies on with pressure. The preferred choice of the material indicated for the strips and the pads has the effect that the bandage offers a high level of wear comfort and requires little retensioning. Furthermore, the selected materials result in an appealing design.

BRIEF DESCRIPTION OF THE FIGURES

With the aid of the figures described below, a particularly advantageous embodiment of the clavicle bandage is illustrated, without wishing thereby to subject the invention to any unnecessary restriction.

DETAILED DESCRIPTION OF THE INVENTION

Figure 1:
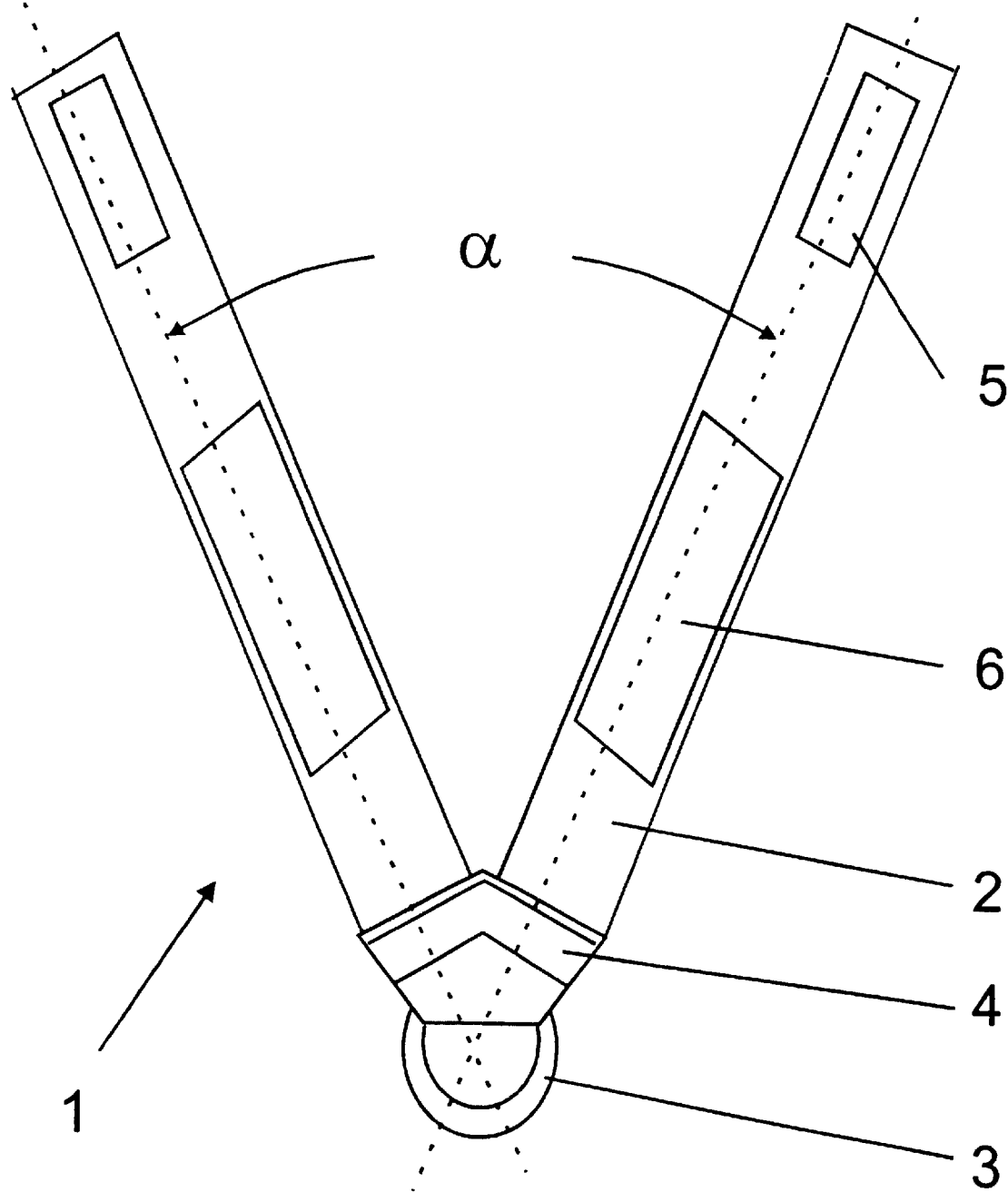
FIG. 1 shows the clavicle bandage in a particularly advantageously configured embodiment.

FIG. 1 shows the clavicle bandage 1 of the invention with the two adjustable-length strips 2 which at their free ends have means 5 of forming loops. The means 5 are designed as a touch-and-close system such that there is a hook section 5 at each free end of the strips 2 on their exterior surface facing away from the body, the said sections 5 each forming one closure part of the touch-and-close fastening and being fastened thereto when the bandage 1 is applied.

With the other end, the strips 2 are fastened to a ring 3 which has a flat elliptical cross section. The fixing of the strips 2 on the ring 3 is accomplished by a material pocket 4, which is configured in the form of a slightly distorted pentagon.

Between the strips 2, therefore, there is an angle α of approximately 68°.

Furthermore, the strips 2, approximately in the middle section of their inner side facing the body, have pads 6 comprising a sweat-absorbing material, preferably comprising a spacer knit made of polyester, nylon and/or cotton, and optionally an additional ply, in order to increase the wear comfort of the patient in the region of the axillae.

Not only the strips 2 themselves but also the hook sections 5 and the pads 6 as well are preferably rectangular in shape. Other embodiments of the bandage may comprise the pads 6 being covered by an additional ply 7 that faces the axillary part of the body.

Figure 2:
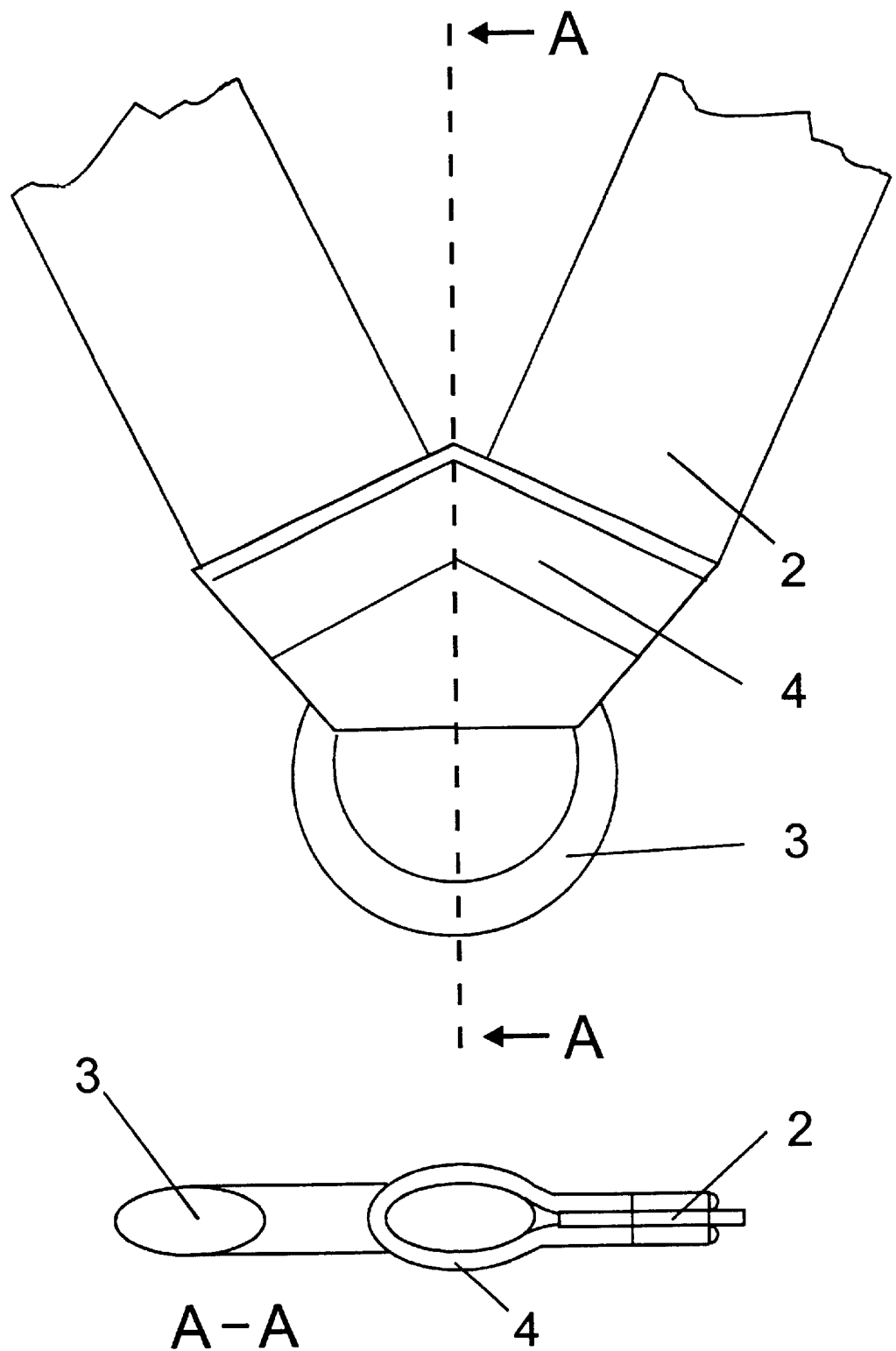
FIG. 2 shows details of the material pocket which positions the strips on the ring, and shows a lateral section along the line A—A through this region of the bandage.

In FIG. 2, the pentagonally shaped material pocket 4 which holds the strips 2 on the ring 3 is shown in detail, along with a lateral section along the line A—A through this region of the bandage 1.

The material pocket 4 preferably comprises a single piece of material into which the ring 3 is placed, after which the piece of material is folded over to form the material pocket 4. Before the material pocket 4 is sewn up, the two strips 2 are introduced and fixed by one or more stitches. The strips 2 are therefore fixed, and the angle α is set. Despite this, the ring 3 is able to rotate in the material pocket 4.

Furthermore, FIG. 2 shows a lateral section along the line A—A through the bandage 1. The section reveals the elliptical cross section of the ring 3 and also the disposition of the strips 2 in the pocket 4.

Figure 3:
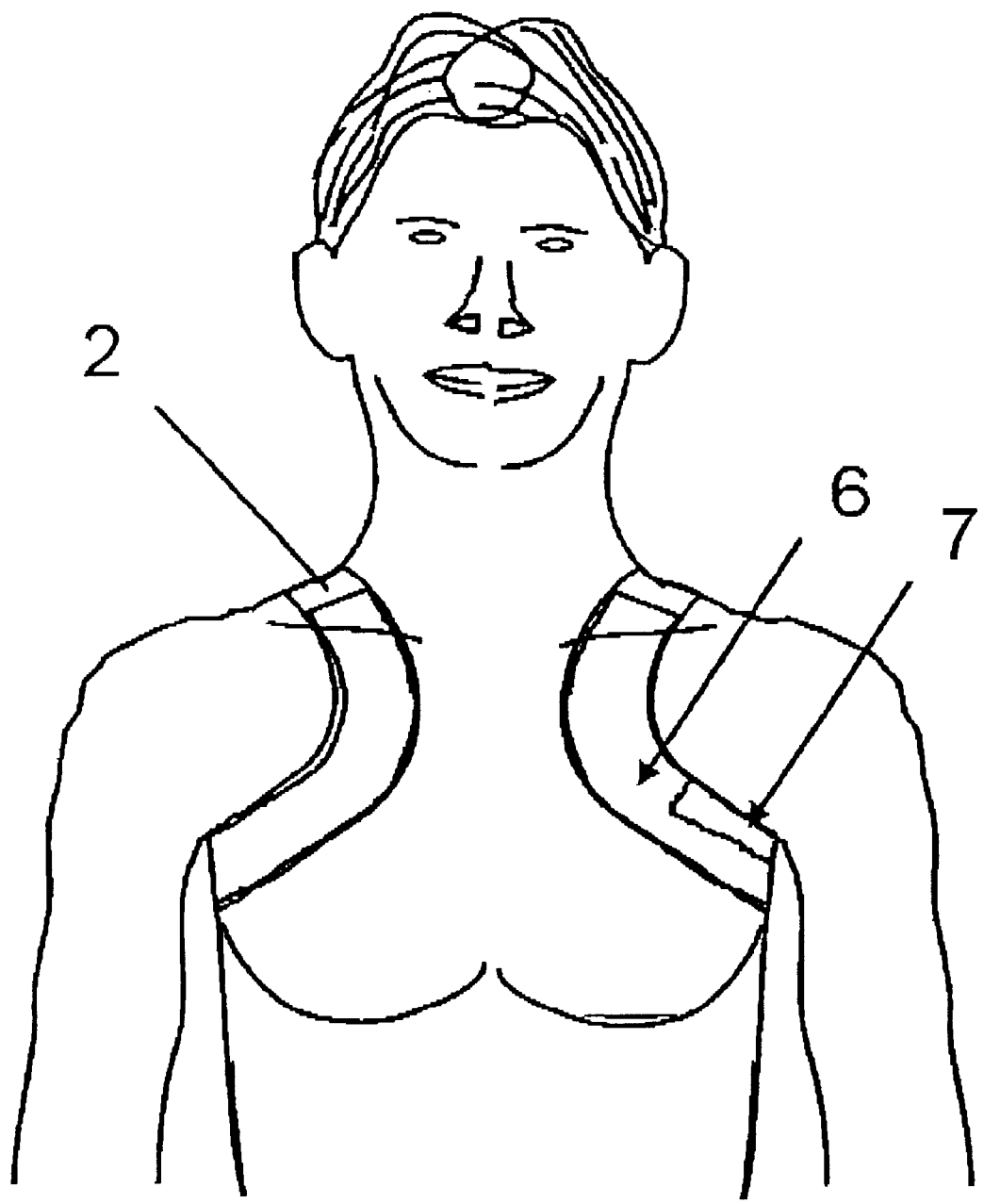
FIG. 3 shows an anterior view of the clavicle bandage applied to the human body.
Figure 4:
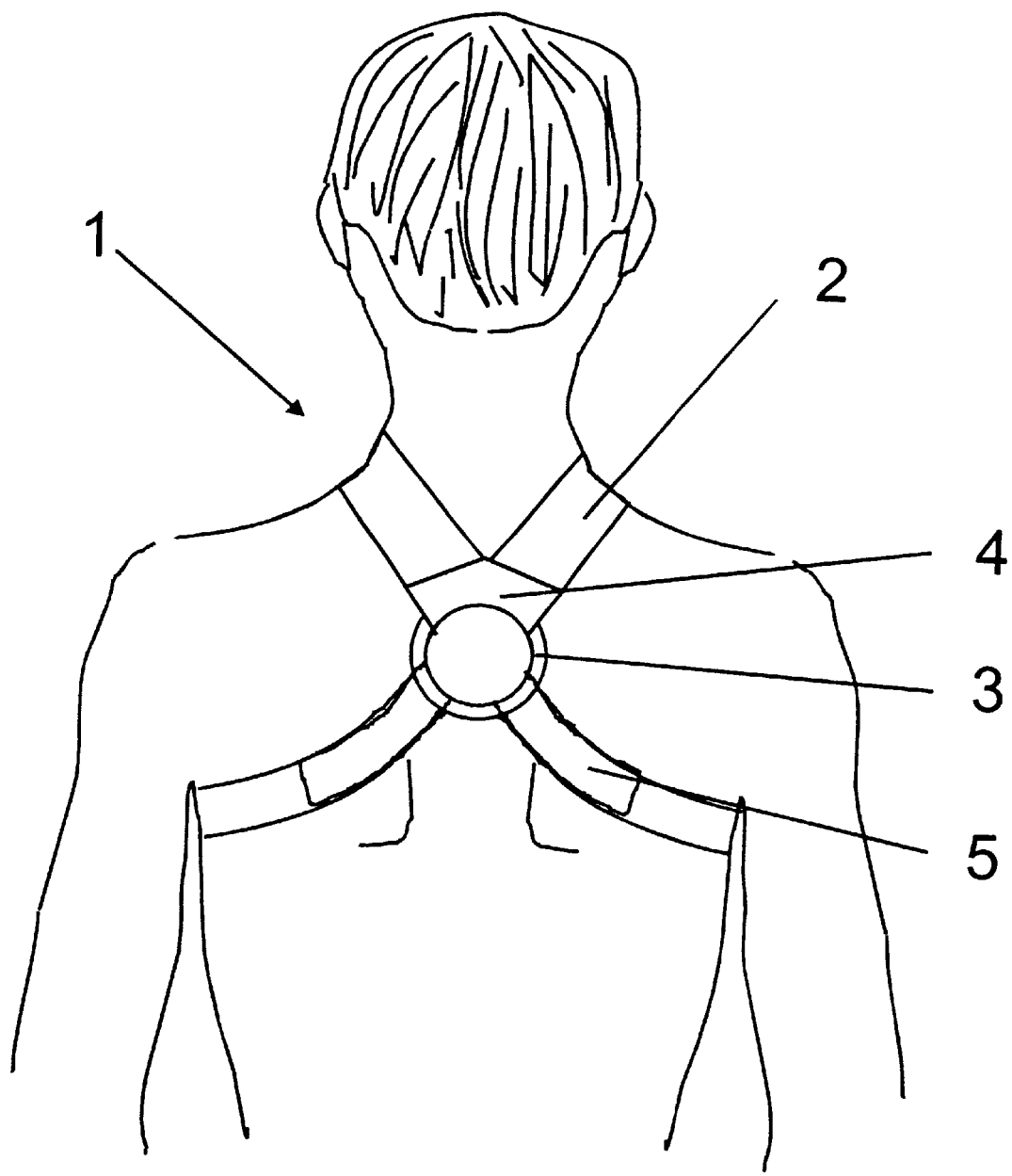
FIG. 4 shows a posterior view of the clavicle bandage applied to the human body.

FIGS. 3 and 4, finally, show the clavicle bandage 1 applied to the human body, from the anterior and posterior respectively.

The bandage 1 is applied by placing the ring 3 on the back of the patient and passing the free ends of the strips 2 over the collarbones. Via the axillae, the free ends of the strips 2 are passed through back again to the ring 3. Beginning with the strip 2, which lies over the undamaged collarbone, the strips 2 are passed through the ring 3, in such a way that the strips 2 are moved away from the body. Finally, the ends of the strips 2 are fastened onto the strips 2 themselves, by means of the hook ends 5, so that by virtue of the resulting loops the ring 3 is fixed in its position on the back.

If desired, the bandage 1 can be readjusted by briefly opening the loops again in order to ensure the required pressure and the desired seating of the bandage.

What is claimed is:

1. A clavicle bandage comprising:
   a) a ring composed of a non-stretchable material having a flat elliptical cross-section;
   b) two adjustable-length strips made essentially of non-extensible material, each of said strips having a fixed end and a free end, the fixed end of each of said strips being attached to a material pocket, and wherein the free end of each of said strips being extended around said ring and is releasably secured to another portion of each of the respective strips, and wherein the length of said strips constitute the only adjustable feature of the bandage; and
   c) the material pocket having the form of a pentagon, wherein one side of said pentagon maintains the ring in a flat and freely rotatable position against the wearer's back, and at other sides of said pentagon, the strips lead away from the ring at an angle of 60° to 80°, and
wherein said ring's freely rotatable feature allows said ring to automatically adjust to a position flat against a wearer's back in response to varying tension resulting from adjustment of the length of one or both of said strips.

2. The clavicle bandage according to claim 1, wherein the free end of each of said strips is releasably secured by a touch-and-close system.

3. The clavicle bandage according to claim 2, wherein the touch-and close system is designed such that the free end of each strip comprises a hook section on an outer surface thereof intended to face away from the body of a user of the bandage, each hook section comprises outwardly directed hooks disposed at a distance from one another, and at least one subsection of the outer surface also carries hookable material to which the hooks are able to adhere.

4. The clavicle bandage according to claim 1, wherein the material pocket has the form of an irregular pentagon and the strips are fixed thereto so that the angle ($\alpha$) between the strips is about 68°.

5. The clavicle bandage according to claim 1, wherein the strips have a pad comprising a sweat-absorbing material at a point approximately in a middle section of a side thereof intended to face the body of a user of the bandage.

6. The clavicle bandage according to claim 5, wherein the sweat-absorbing material comprises polyester, nylon and/or cotton.

7. The clavicle bandage according to claim 5, wherein the pad comprises a spacer knit with a thickness of from 3.5 mm to 15 mm and a basis weight of from 200 to 1000 g/m$^2$, and the pad is roughened on a surface of the side of the pad which is intended to face the body of a user of the pad.

8. The clavicle bandage according to claim 7, wherein the spacer knit is covered with an additional ply on the side of the pad which is intended to face the axillary part of the body of a user of the pad.

* * * * *